(12) United States Patent
Gharagozloo

(10) Patent No.: US 7,868,299 B2
(45) Date of Patent: Jan. 11, 2011

(54) SYSTEMS AND METHODS FOR ADJUSTABLY DETECTING ULTRA-VIOLET RADIATION

(75) Inventor: Mahmood Gharagozloo, North Potomac, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 157 days.

(21) Appl. No.: 12/289,133

(22) Filed: Oct. 21, 2008

(65) Prior Publication Data

US 2010/0096534 A1    Apr. 22, 2010

(51) Int. Cl.
*G01J 1/42*    (2006.01)
(52) U.S. Cl. ...................................................... 250/372
(58) Field of Classification Search .................. 250/372
See application file for complete search history.

(56) References Cited

U.S. PATENT DOCUMENTS

| | | | | |
|---|---|---|---|---|
| 4,629,896 A * | 12/1986 | Bridgen | ...................... | 250/372 |
| 5,412,133 A * | 5/1995 | Eckberg | ...................... | 556/427 |
| 7,244,946 B2 * | 7/2007 | Burnette et al. | ............. | 250/372 |
| 7,401,943 B2 | 7/2008 | Okamitsu et al. | | |
| 2003/0227527 A1 * | 12/2003 | Richards | ...................... | 347/102 |
| 2004/0257234 A1 * | 12/2004 | Stebbings | ................... | 340/578 |

OTHER PUBLICATIONS

Bae et al., "UV detecting properties of ZnO-based thin film transistors," 2004, Thin Solid Films, Vo. 469-470, pp. 75-79.*
M. Topic, "Adjustable UV-sensitive detectors based on amorphous silicion," 2001, Applied Physics Letters, Vo. 78, No. 16, pp. 2387-2389.*
Honeywell, C7076A, D Adjustable Sensitivity Ultraviolet Flame Detector, 2002, Product Data.*
Horowitz et al., "The Art of Electronics", 1989, second edition, pp. 344.*
"Electrodeless Lamp" from Wikipedia, http://en.wikipedia.org/wiki/Electrodeless_lamp, accessed on Aug. 5, 2008, 8 pages.
"Ultraviolet Germicidal Irradiation" from Wikipedia, http://en.wikipedia.org/wiki/Ultraviolet_germicidal_irradiation, accessed on Aug. 5, 2008, 9 pages.

* cited by examiner

*Primary Examiner*—David P Porta
*Assistant Examiner*—Kiho Kim
(74) *Attorney, Agent, or Firm*—McDermott Will & Emery LLP

(57) ABSTRACT

The invention disclosed provides an improved method and apparatus for light sensing to detect bulb ignition for UV curing lamps. The light sensing apparatus is configured with adjustable sensitivity, and can be configured for use with a range of light intensity levels. The light sensing apparatus can be configured for use with multiple ultra-violet lamps in a variety of spatial configurations. The light sensing apparatus comprises a phototransistor circuit configured with adjustable sensitivity. The improved apparatus further comprises a signal conditioning circuit.

44 Claims, 9 Drawing Sheets

SYSTEMS AND METHODS FOR ADJUSTABLY DETECTING ULTRA-VIOLET RADIATION

FIELD OF THE INVENTION

The present invention relates to a method and an apparatus for providing substantially improved detection of ultra-violet radiation. More particularly, the present invention pertains to using a phototransistor circuit with adjustable sensitivity to detect bulb ignition in ultra-violet curing lamp systems.

DESCRIPTION OF THE PRIOR ART

Radiant energy is used in a variety of manufacturing processes to treat surfaces, films, coatings, over layers, and bulk materials. Specific processes include but are not limited to curing, fixing, polymerization, oxidation, purification, or disinfections. By way of example, the manufacture of components for motor vehicles involves the application of undercoatings, paints or clear coatings on vehicle surfaces for various purposes including corrosion resistance, decoration or surface protection (e.g. scratch resistance). The coatings or paints are resins or polymer-based materials that are applied as liquids or powders and require thermal or radiant energy processing to become solids. The processing of coatings or paints by thermal methods is slow and requires times ranging from minutes to hours to complete. In addition, some materials (for example, substrates or coating components) may be heat sensitive and damaged by thermal treatments.

Non-thermal curing using radiant energy to polymerize or effect a desired chemical change is rapid in comparison to thermal treatment. Radiation-based curing can also be localized in the sense that curing can preferentially take place where the radiation is applied. Curing can also be localized within the coating or thin film to interfacial regions or in the bulk of the coating or thin film. Control of the curing process is achieved through selection of the radiation source type, physical properties (for example, spectral characteristics), temporal variation, or the curing chemistry (for example, coating composition).

A variety of radiation sources are used for curing, fixing, polymerization, oxidation, purification, or disinfections of a variety of targets. Examples of such sources include but are not limited to photon, electron or ion beam sources. Typical photon beam sources include but are not limited to arc lamps, incandescent lamps, electrodeless lamps and a variety of electronic and solid-state sources (such as, for example, solid state lasers, light-emitting diodes and diode lasers). Selection of a specific radiation source for an application is contingent on the requirements of the treatment process and the characteristics of the radiation source. These characteristics are related to but are not limited to the physical properties of the source, its efficiency, economics, or characteristics of the treatment process or target. For example, arc lamps and radio-frequency or microwave driven "electrodeless" ultra-violet sources efficiently produce high levels of radiated power having applications in many industrial processes where rapid treatment using significant levels of irradiance or energy density over large areas are needed.

Electrodeless ultra-violet lamps transfer power to a bulb by means of electromagnetic fields. For many reasons, including human safety, equipment safety, and customer product integrity, it is important to detect if an ultra-violet lamp is ignited. For example, supplying power to a lamp with an unlit bulb can result in unsafe conditions for human and for equipment. Further, an unlit bulb can have a deleterious effect on product integrity. For example, if undetected, an unlit bulb can cause products passing by the bulb to not be cured properly. Additionally, detecting if a bulb is ignited is important to maintaining system interlock. Interlock requires that all locks be closed, that is, that each vital system component be properly functioning, to allow the system to operate.

Prior art ultra-violet curing systems utilize a light sensor to determine if an ultra-violet bulb in the prior art ultra-violet curing system is ignited. FIGS. 1A and 1B depict prior art light sensors. The light sensor of FIG. 1B is similar to the light sensor of FIG. 1A, except that FIG. 1B includes photoresistor 31, while FIG. 1A includes photodiode 30. In both FIGS. 1A and 1B, photodiode 30 or photoresistor 31 respectively may be connected in series with load resistor 10. Incident radiation 20 strikes photodiode 30 or photoresistor 31, and causes a current to flow through photodiode 30 or photoresistor 31 and a current to flow through load resistor 10. In response to incident radiation 20, and because of the current flowing through photodiode 30 or photoresistor 31 and the current flowing through load resistor 10, a sensor output 40 can be detected. (Here, and throughout, "sensor output" refers to a voltage signal available as an output of a light sensor. As is known in the art, a current signal could be used instead of a voltage signal.) The output signal at sensor output terminal 40 depends on the magnitude of the current flowing through load resistor 10. The magnitude of the current flowing through load resistor 10 in turn depends on the intensity of incident radiation 20. Therefore, the output signal at sensor output 40 can provide information about the intensity of incident radiation 20. This information can be used to determine if the ultra-violet bulb is ignited.

The prior art systems used a photodiode or photoresistor in the light sensor, where the photodiode or photoresistor cannot provide for an adjustable gain. Because the photodiode or photoresistor gain cannot be adjusted, the sensor output for a given incident radiation intensity cannot easily be adjusted. (Throughout, "adjusting sensitivity" and like terms will be used to refer to varying the sensor output for a given incident radiation intensity.) By incorporating welding glass into the prior art ultra-violet curing system, prior art light sensors can be modified to permit some adjustment of sensitivity. For example, in current systems, welding glass may be incorporated into the prior art light sensor. The welding glass may be placed between the light source and the photodiode or photoresistor, thereby forcing all incident radiation that reaches the photodiode or photoresistor to first pass through the welding glass. The welding glass transmits only a fraction of the light that is incident upon the welding glass. By varying the thickness, color, or composition of the glass, the fraction of the incident light that is transmitted can be varied, thereby varying the radiation intensity that is incident upon the photodiode or photoresistor. By this varying of the incident radiation intensity, some adjustment of sensitivity is possible. Although this process provides some adjustment of sensitivity, the process requires imprecise and time consuming calibration.

Because the sensitivity of the prior art light sensor cannot be easily adjusted, problems may arise. For example, operators may want to operate an ultra-violet lamp through a wide range of power levels and intensities. Because the prior art light sensor's sensitivity cannot be easily adjusted, the prior art light sensor cannot be easily adapted for use with light sources having different power levels and intensities. As a second example, problems can arise with the prior art light sensor when using multiple ultra-violet lamps in combination. For example, in a system with two ultra-violet lamps situated near each other, the first lamp's bulb can be ignited while the second lamp's bulb is not ignited. In such a system, the scattered light from the ignited first lamp may provide scattered incident radiation to the prior art light sensor in the non-ignited second lamp. The scattered incident radiation may be of sufficient intensity to cause the prior art light sensor of the non-ignited second lamp to incorrectly signal the state of the second lamp (that is, the prior art light sensor of the non-ignited second lamp may signal that the non-ignited second lamp is ignited). The inability to easily adjust the sensitivity of the prior art light sensor prevents easily adjusting the sensitivity to overcome the problem posed by scattered incident radiation. Because of this incorrect signaling, some failure modes may go undetected.

SUMMARY OF THE INVENTION

The present invention provides an improved method and apparatus for light sensing to detect bulb ignition for ultraviolet curing lamps. The invention provides for a method for detecting radiant energy with a light sensing apparatus. The light sensing apparatus comprises a phototransistor circuit configured with adjustable sensitivity and a signal conditioning circuit. The invention provides for the light sensing apparatus to be configured for use with a range of light intensity levels. The invention further provides for the light sensing apparatus to be configured for use with multiple ultra-violet lamps in a variety of spatial configurations.

In one embodiment the light sensing apparatus comprises a three terminal phototransistor comprising a base, a collector, and an emitter. The three terminal transistor may, for example, be a bipolar junction transistor. The light sensing apparatus further comprises a circuit for adjusting the sensitivity of the phototransistor circuit. In an embodiment the circuit for adjusting sensitivity may comprise a resistor-capacitor circuit, with a variable resistor. If a variable resistor (such as a potentiometer) is used, the sensitivity of the phototransistor circuit can be adjusted by varying the potentiometer resistance. Alternatively, if the desired sensitivity is known during the manufacturing of the light sensing apparatus, the sensitivity can be adjusted during the manufacturing of the light sensing apparatus through the use of a fixed resistor of appropriate resistance.

The light sensing apparatus further comprises a signal conditioning circuit. In any embodiment, the signal conditioning circuit could comprise a low-pass filter circuit. In any such embodiment, the low-pass filter circuit may comprise a resistor-capacitor circuit. For example, if the light intensity varies as a function of time, such as might occur where the ultra-violet lamp receives power from a conventional 60 Hz AC power source, a signal conditioning circuit comprising a low-pass filter can "smooth out" any 60 Hz variation that would otherwise be present.

The present invention also provides for a UV lamp system comprising a first lamp configured to provide a first lamp operational radiation output to an output region when in a first lamp operating state, and where the first lamp further provides less than the first lamp operational radiation output to the output region when in a first lamp failure state. The UV lamp system further comprises a second lamp configured to provide a second lamp operational radiation output to the output region when in a second lamp operating state, and where the second lamp provides less than the second lamp operational radiation output to the output region when in a second lamp failure state. Radiation from the second lamp in the output region may be direct radiation or reflected radiation. The UV lamp system contains a light sensing apparatus comprising a phototransistor circuit with an adjustable sensitivity configured to provide signals based on the states of the first and second lamp as detected by the light sensing apparatus. The sensitivity of the phototransistor circuit may be adjusted to achieve the desired signals based on the state of the first lamp and the state of the second lamp.

The present invention also provides for a UV lamp system comprising a first lamp configured to provide a first lamp operational radiation output to an output region when in a first lamp operating state, and where the first lamp further provides less than the first lamp operational radiation output to the output region when in a first lamp failure state. The UV lamp system further comprises a light sensing apparatus comprising a phototransistor circuit with an adjustable sensitivity configured to provide signals based on the state of the first lamp. The sensitivity of the phototransistor circuit may be adjusted to achieve the desired signals based on the state of the first lamp.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts.

The present invention provides for a method for detecting radiant energy with a light sensing apparatus. In the present invention the light sensing apparatus comprises a phototransistor circuit. The light sensing apparatus further comprises a signal conditioning circuit. The signal conditioning circuit receives a signal from the phototransistor circuit. The signal conditioning circuit conditions the signal received from the phototransistor circuit and provides a sensor output based upon the signal received from the phototransistor circuit. The conditioning may, for example, comprise conditioning to meet voltage, current, or timing requirements. The conditioning may comprise filtering, including, for example, low pass filtering. The output signal of the signal conditioning circuit can be accessed on a sensor output terminal. (The output signal which is accessible on the sensor output terminal will be called the sensor output.) The sensor output may be detected or utilized by other systems.

The phototransistor circuit of the light sensing apparatus is configured with an adjustable sensitivity. In an embodiment, the phototransistor circuit comprises a three terminal phototransistor comprising a base, an emitter, and a collector. The phototransistor may, for example, be a bipolar junction transistor. The phototransistor circuit further comprises an adjustable sensitivity circuit. The adjustable sensitivity circuit may comprise a parallel coupled capacitor and an adjustable resistance, coupled between the base and a ground terminal. The adjustable resistance may, for example, be a potentiometer. The adjustable resistance may also be a fixed resistor capable of being removed and replaced by a different resistor. The sensitivity of the phototransistor circuit can be adjusted by changing the value of the adjustable resistance. An example of an adjustable sensitivity circuit will be illustrated and described below in reference to FIG. 2.

Figure 5:
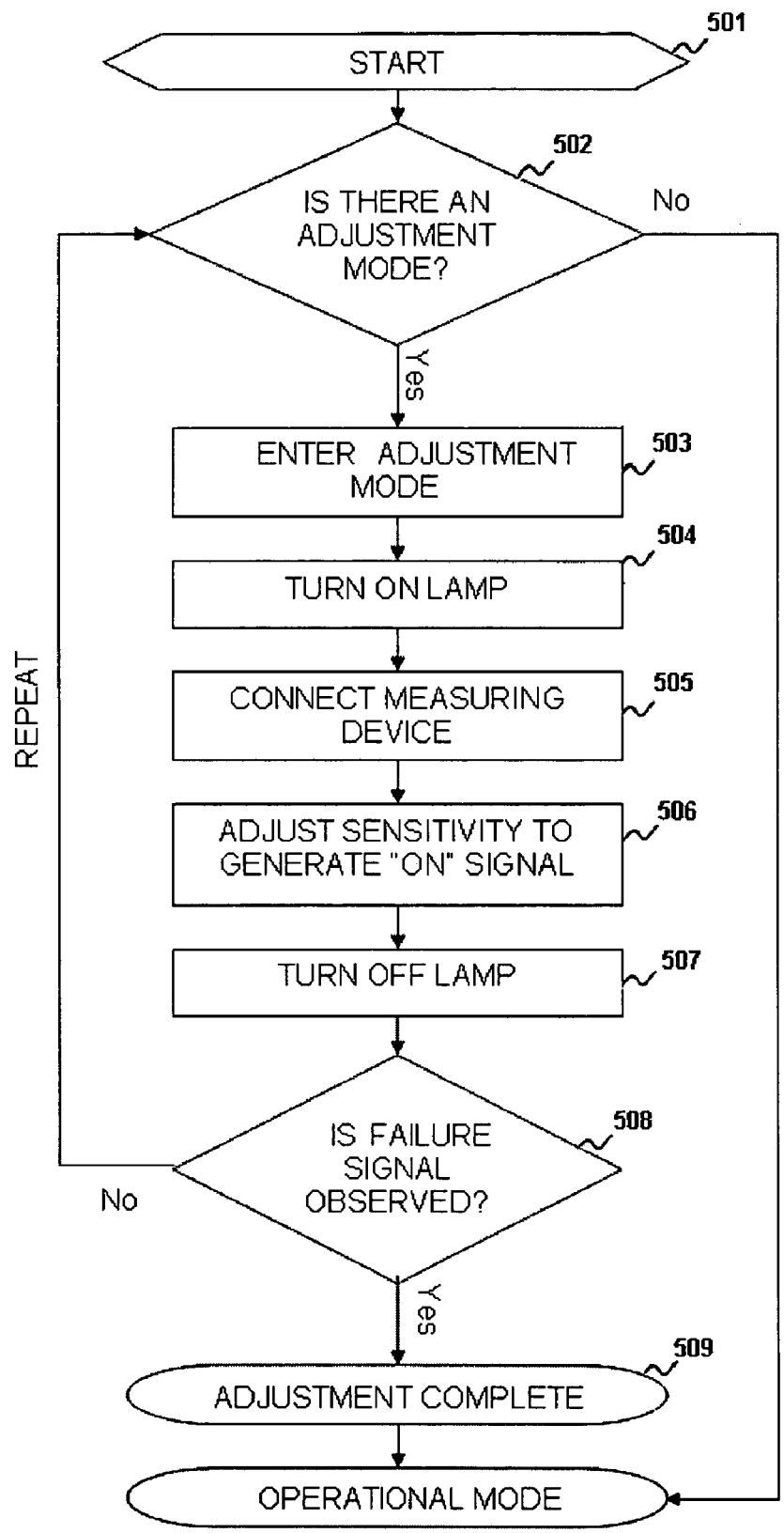
FIG. 5 is a flow chart of steps performed in an adjusting process, consistent with an embodiment of the present invention.

The sensitivity of the phototransistor circuit can be adjusted for detecting a range of incident light intensities. The sensitivity of the phototransistor circuit can also be adjusted for detecting a variety of conditions in a variety of systems. For example, in one embodiment, the sensitivity of the phototransistor circuit can be adjusted for use during operation of an ultra-violet lamp system. The phototransistor circuit can be operated to detect light from the ultra-violet lamp and maintain this detection during the operation of the ultra-violet lamp. The phototransistor circuit can give an "ON" signal while the ultra-violet lamp is emitting light and a failure signal when the ultra-violet lamp is not emitting light (Hardware or software for other parts of the system may set a threshold value for an "ON" signal and for an failure signal). The "ON" or failure signal can be received and conditioned by the signal conditioning circuit. The sensitivity of the phototransistor circuit can be adjusted to meet the aforementioned requirements. As illustrated in FIG. 5, to meet the requirements, the following steps may be taken to adjust the sensitivity (beginning at step 501) of the phototransistor circuit:

1) If necessary (step 502), an adjustment mode 503 may be entered. While in the adjustment mode, the ultra-violet lamp will be configured to allow the ultra-violet lamp to operate while the adjustment is in process.
2) The ultra-violet lamp may be turned on (step 504). If the ultra-violet lamp has an modifiable power level, the ultra-violet lamp may be modified to a power level for the desired application (that is, the power level may be modified for the application for which the sensitivity of the phototransistor circuit is being adjusted).
3) A multi-meter or other voltage measuring device may be connected (step 505) to measure the sensor output (which is available at the sensor output terminal). This signal will be observed while the sensitivity of the phototransistor circuit is adjusted. (One skilled in the art would appreciate that the connection of the measuring device does not have to occur in this precise sequence in order to be consistent with the present invention.)
4) The sensitivity of the phototransistor circuit may be adjusted (step 506) to create the desired "ON" signal (that is, the sensitivity of the phototransistor circuit may be adjusted until the sensor output is at the desired level). Hardware or software for other parts of the system may set a threshold value for detecting an "ON" signal. In one embodiment, the phototransistor circuit can be adjusted so the sensor output level is beyond this threshold by a safety margin, e.g. 0.5 VDC. (The sensor output level may be adjusted above or below the threshold value respectively depending if the light sensing apparatus is inverting or non-inverting. Such adjustment would be understood by one of ordinary skill in the art.)
5) The ultra-violet lamp may then be turned off (step 507). The sensor output will be observed to ensure that the sensor output now provides the failure signal (step 508). (If the first light sensing apparatus does not provide the failure signal, steps 1-4 should be repeated). If sensor output now provides the failure signal, the adjustment is complete (step 509).

After adjustment, the ultra-violet lamp may enter an "operational mode" in which the lamp may be used for ultra-violet curing. The aforementioned procedure can be repeated for multiple lamps. The aforementioned adjustment process could be completed by a customer who purchased an ultra-violet lamp system including a light sensing apparatus with an adjustable sensitivity. Alternatively, if the customer provided necessary information including the power level for the desired application, the desired sensor output level for the "ON" signal, and the desired sensor output level for the failure signal, the aforementioned adjustment process could be completed by a manufacturer of an ultra-violet lamp system.

Figure 6:
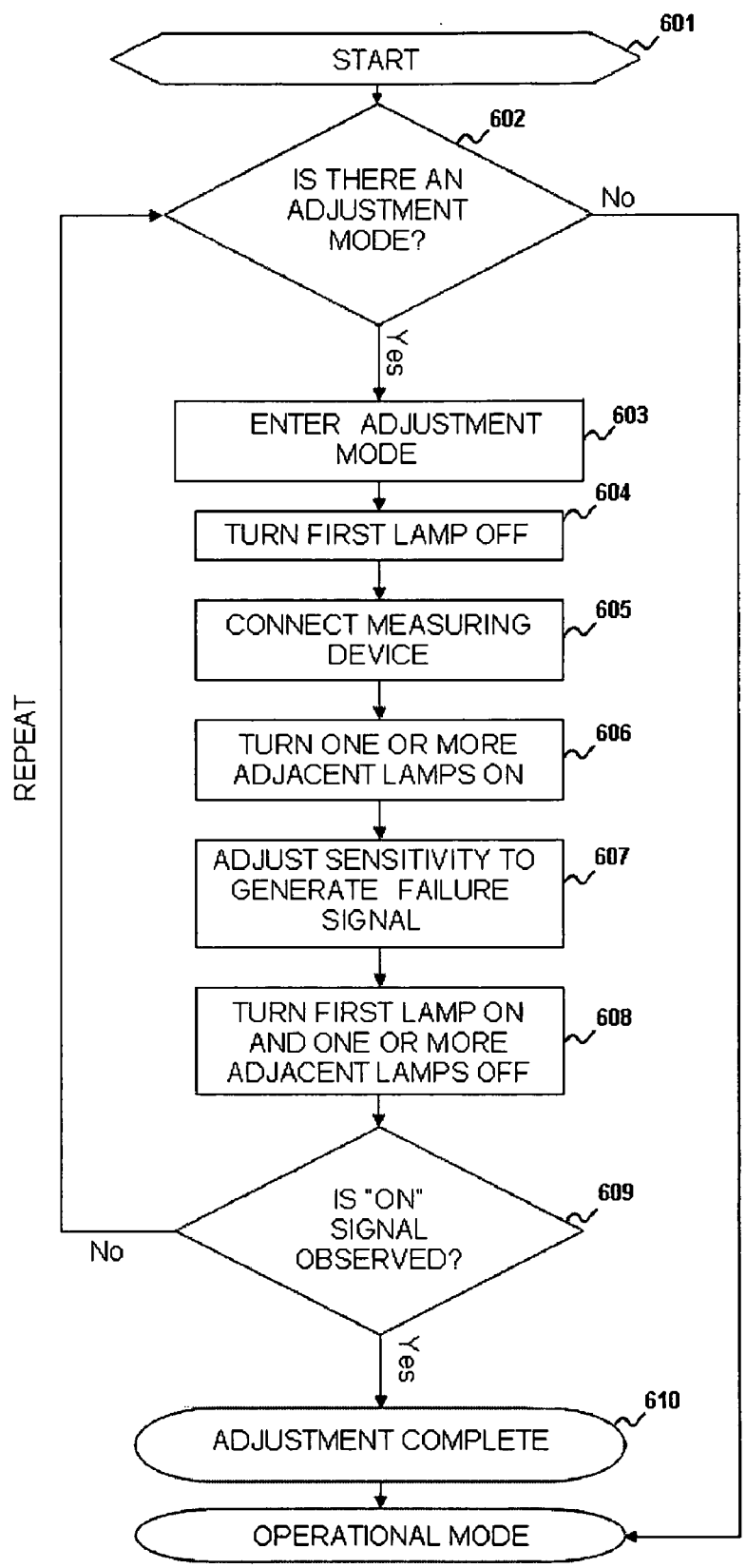
FIG. 6 is a flow chart of steps performed in another adjusting process, consistent with an embodiment of the present invention.

In another embodiment, the sensitivity of the phototransistor circuit can be adjusted for use with multiple ultra-violet lamps. The use of the phototransistor circuit with adjustable sensitivity would help to insure the proper operation of the lamps when there is possibility of light emitted from a lamp to satisfy the light sensor in the adjacent lamp. The phototransistor circuit with adjustable sensitivity may be adjusted so that the circuit can give an "ON" signal while a first ultra-violet lamp is emitting light and a failure signal when the first ultra-violet lamp is not emitting light, regardless of the state of any adjacent lamps. As illustrated in FIG. 6, to meet the requirements for adjusting the sensitivity (beginning at step 601) of the phototransistor of the first ultra-violet lamp, the following steps may be taken:

1) If necessary, (step 602) an adjustment mode may be entered (step 603). While in the adjustment mode, the first ultra-violet lamp will be configured to allow the ultra-violet lamp to operate while the adjustment is in process.
2) At step 604, the first ultra-violet lamp is turned off (that is, the bulb of the first ultra-violet lamp emits no radiation).
3) A multi-meter or other voltage measuring device may be connected (step 605) to measure the output signal (which is available at the sensor output). This signal will be observed while the sensitivity of the phototransistor circuit is adjusted. (One skilled in the art would appreciate that the connection of the measuring device does not have to occur in this precise sequence in order to be consistent with the present invention.)
4) At step 606, one or more adjacent lamps are turned on (that is, the bulbs of the one or more adjacent lamps are set to emit light). If the output power of the one or more adjacent lamps is adjustable, the output power of the one or more adjacent lamps is adjusted to the power level that will be used in the process. If more than one power level is used, the power level is adjusted to the highest level.

5) The sensitivity of the phototransistor circuit may be adjusted (step 607) to create the desired failure signal (that is, the sensitivity of the phototransistor circuit may be adjusted until the sensor output is at the desired level). Hardware or software for other parts of the system may set a threshold value for detecting a failure signal. In one embodiment, the phototransistor circuit can be adjusted so the sensor output level is beyond this threshold by a safety margin, e.g. 0.5 VDC. (The sensor output level may be adjusted above or below the threshold value respectively depending if the light sensing apparatus is inverting or non-inverting. Such adjustment would be understood by one of ordinary skill in the art.)

6) The first ultra-violet lamp may then be turned on and the one or more adjacent lamps are turned off (step 608). The sensor output will be observed to ensure that the sensor output now provides the "ON" signal (step 609). (If the first light sensing apparatus does not provide the "ON", steps 1-5 should be repeated). If the sensor output now provides the "ON" signal, the adjustment is complete (step 610).

After adjustment, the ultra-violet lamp may enter an "operational mode" in which the lamp may be used for ultra-violet curing. The aforementioned procedure can be repeated for multiple lamps. The aforementioned adjustment process could be completed by a customer who purchased an ultra-violet lamp system including a light sensing apparatus with an adjustable sensitivity. Alternatively, if the customer provided necessary information including the power level for the desired application, the number and spatial configuration of adjacent ultra-violet lamps, the desired sensor output level for the "ON" signal, and the desired sensor output level for the failure signal, the aforementioned adjustment process could be completed by a manufacturer of an ultra-violet lamp system including a light sensing apparatus with an adjustable sensitivity.

As mentioned above, the light sensing apparatus comprises a signal conditioning circuit. The signal conditioning circuit receives a signal from the phototransistor circuit. The signal conditioning circuit conditions the signal received from the phototransistor circuit, and the signal conditioning circuit provides the sensor output. The signal conditioning circuit may, for example, condition the signal received from the phototransistor circuit to meet voltage, current, or timing requirements. Additionally, because the ultra-violet lamp may draw power from an AC source, the light output of the ultra-violet lamp may exhibit an AC oscillation (e.g., an oscillation at 60 Hz). The signal conditioning circuit may include a lowpass filter for reducing undesirable high frequency noise. In one embodiment the signal conditioning circuit may comprise a resistor coupled between the collector and the sensor output terminal. The signal conditioning circuit may further comprise a capacitor coupled between the emitter and the sensor output terminal, wherein a first end of the capacitor is coupled to the emitter and a second end of the capacitor is coupled to the sensor output terminal. The emitter and the first end of the capacitor may further be coupled to the ground terminal.

Figure 1A:
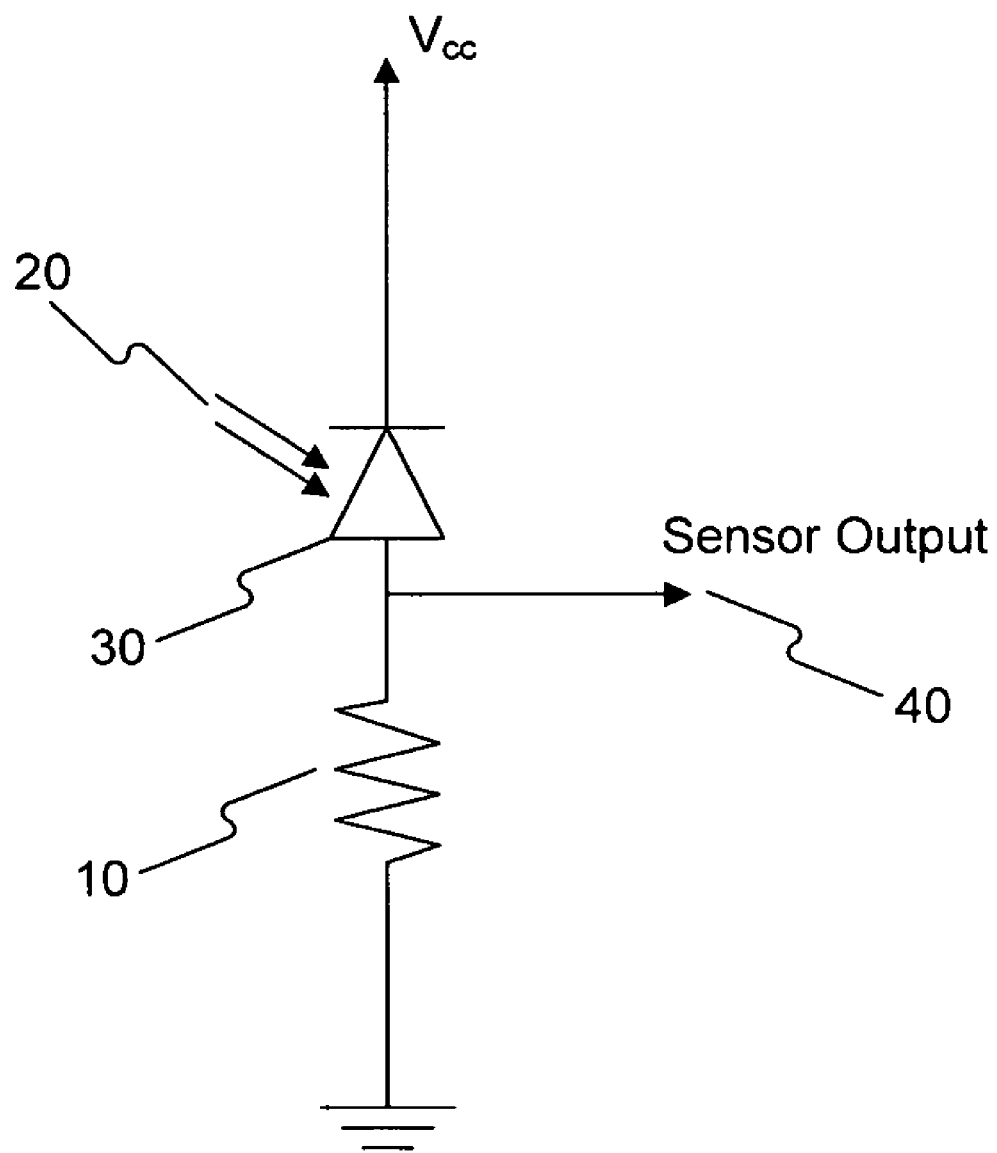
FIGS. 1A and 1B depict prior art light sensing circuits.
Figure 1B:
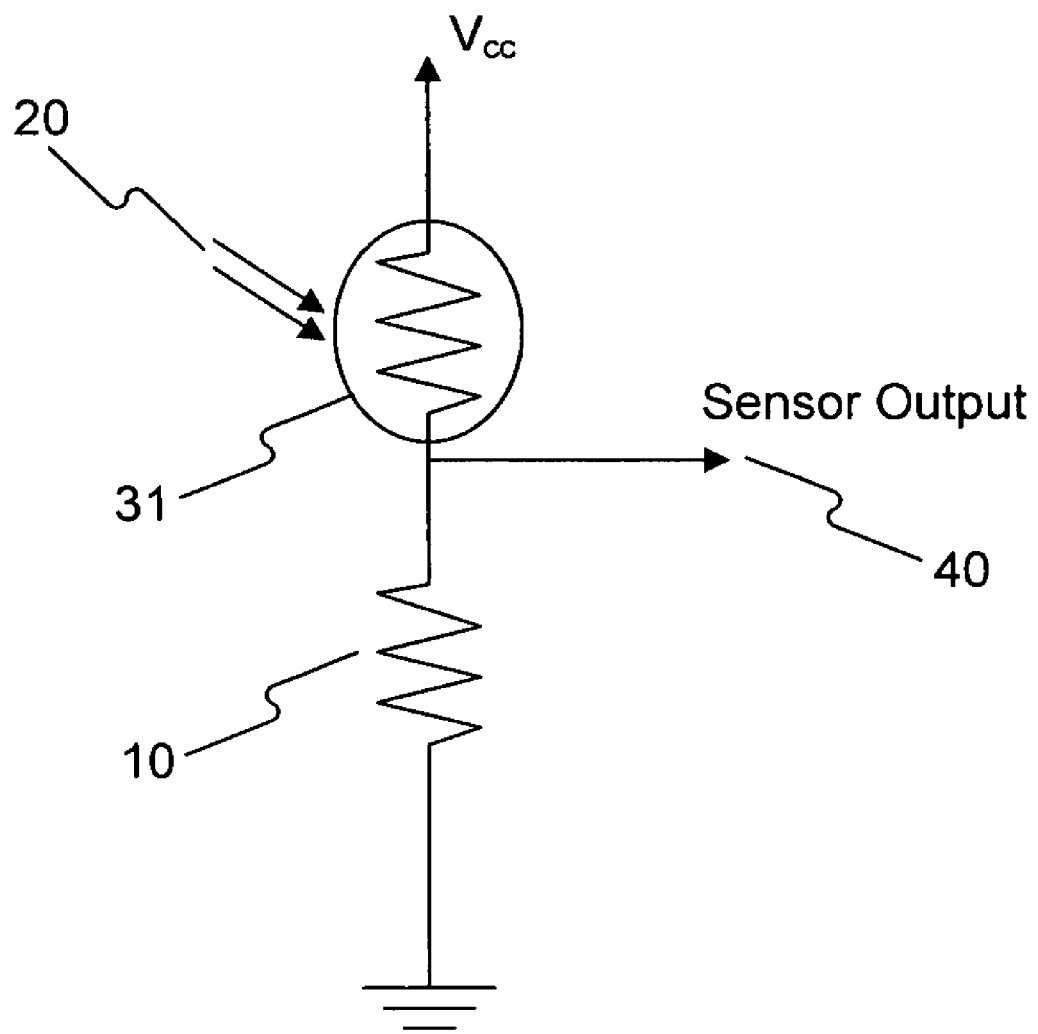
Figure 2:
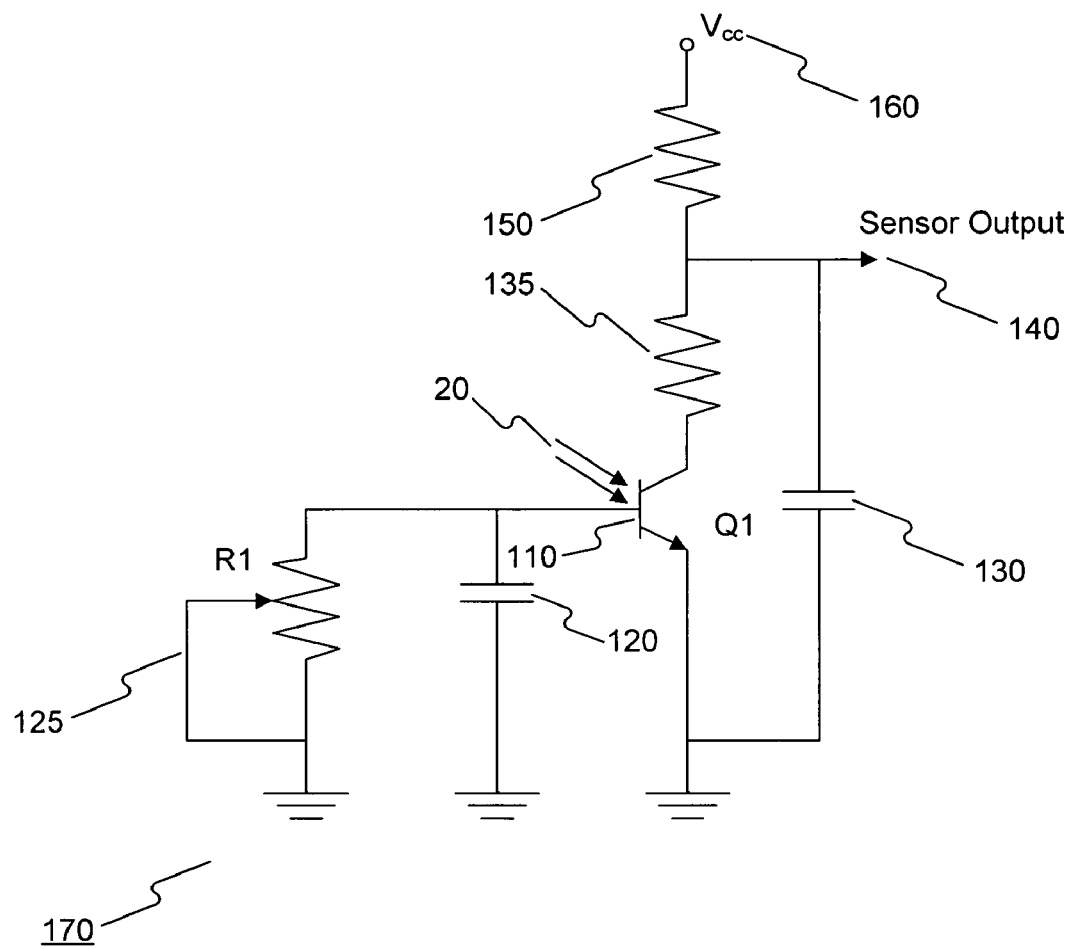
FIG. 2 is an adjustable light sensing circuit consistent with an embodiment of the present invention.

An embodiment of a circuit consistent with the present invention is shown in FIG. 2. In FIG. 2 a light sensing apparatus 170 comprises a phototransistor circuit configured with an adjustable sensitivity. The sensitivity of the phototransistor circuit can be adjusted for detecting a range of light intensities. The sensitivity of the phototransistor circuit can also be adapted for use with multiple lamps in varied orientations. The phototransistor circuit comprises a three terminal phototransistor 110 comprising a base, an emitter, and a collector. The phototransistor 110 is struck by incident radiation 20. The phototransistor circuit further comprises an adjustable sensitivity circuit, comprising a first parallel coupled capacitor 120 and an adjustable resistance 125, coupled between the base and a ground terminal. The adjustable resistance 125 may, for example, be a potentiometer. The adjustable resistance 125 may also be a fixed resistor capable of being removed and replaced by a different resistor. The sensitivity of the phototransistor circuit can be adjusted by changing the value of the adjustable resistance 125.

The light sensing apparatus 170 of FIG. 2 further comprises a signal conditioning circuit. The signal conditioning circuit may condition a signal received from the phototransistor circuit. The sensor output on the sensor output terminal 140 may be detected or utilized by other systems. The signal conditioning circuit of FIG. 2 comprises a resistor 135 coupled between the collector and the sensor output terminal 140. The signal conditioning circuit further comprises a capacitor 130 coupled between the emitter and the sensor output terminal 140, wherein a first end of the capacitor 130 is coupled to the emitter and a second end of the capacitor 130 is coupled to the sensor output terminal 140. The emitter and the first end of the capacitor 130 are further be coupled to the ground terminal. Finally, the embodiment of FIG. 2 comprises a pull-up resistor 150 coupled between sensor output terminal 140 and a voltage rail 160.

Figure 3:
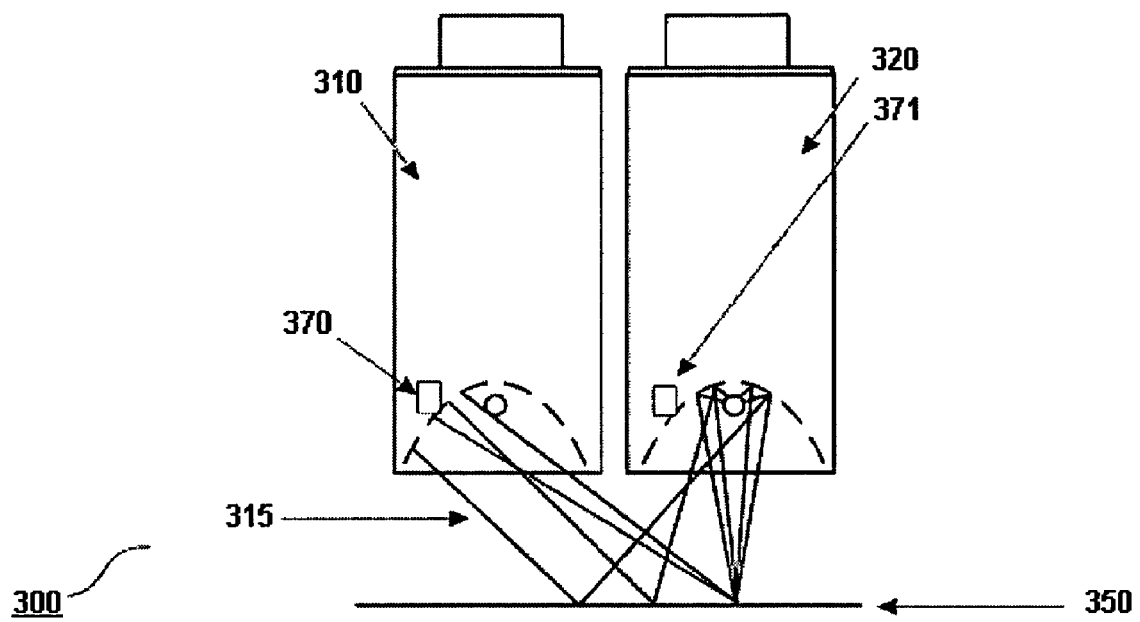
FIG. 3 is a UV lamp system consistent with an embodiment of the present invention.

An embodiment of a UV lamp system 300 consistent the present invention is shown in FIG. 3. The UV lamp system 300 comprises a first lamp 310 with a first light sensing apparatus 370. Although first light sensing apparatus 370 is depicted as contained within first lamp 310, this need not necessarily be true. First light sensing apparatus 370 could be outside first lamp 310. UV lamp system 300 further comprises a second lamp 320. UV lamp system 300 may, but need not necessarily, comprise a second light sensing apparatus 371. Although second light sensing apparatus 371 is depicted as contained within second lamp 320, this need not necessarily be true. Second light sensing apparatus 371 could be outside second lamp 320. As shown in FIG. 3, first lamp 310 and second lamp 320 are substantially parallel and adjacent. In UV lamp system 300, first lamp 310 is configured to provide a first lamp operational radiation output to an output region when in a first lamp operating state. First lamp 310 is further configured to provide less than the first lamp operational radiation output to the output region when in a first lamp failure state. Similarly, in UV lamp system 300, second lamp 320 is configured to provide a second lamp operational radiation output 315 to an output region when in a second lamp operating state. Second lamp 320 is further configured to provide less than the second lamp operational radiation output to the output region when in a second lamp failure state.

Figure 7:
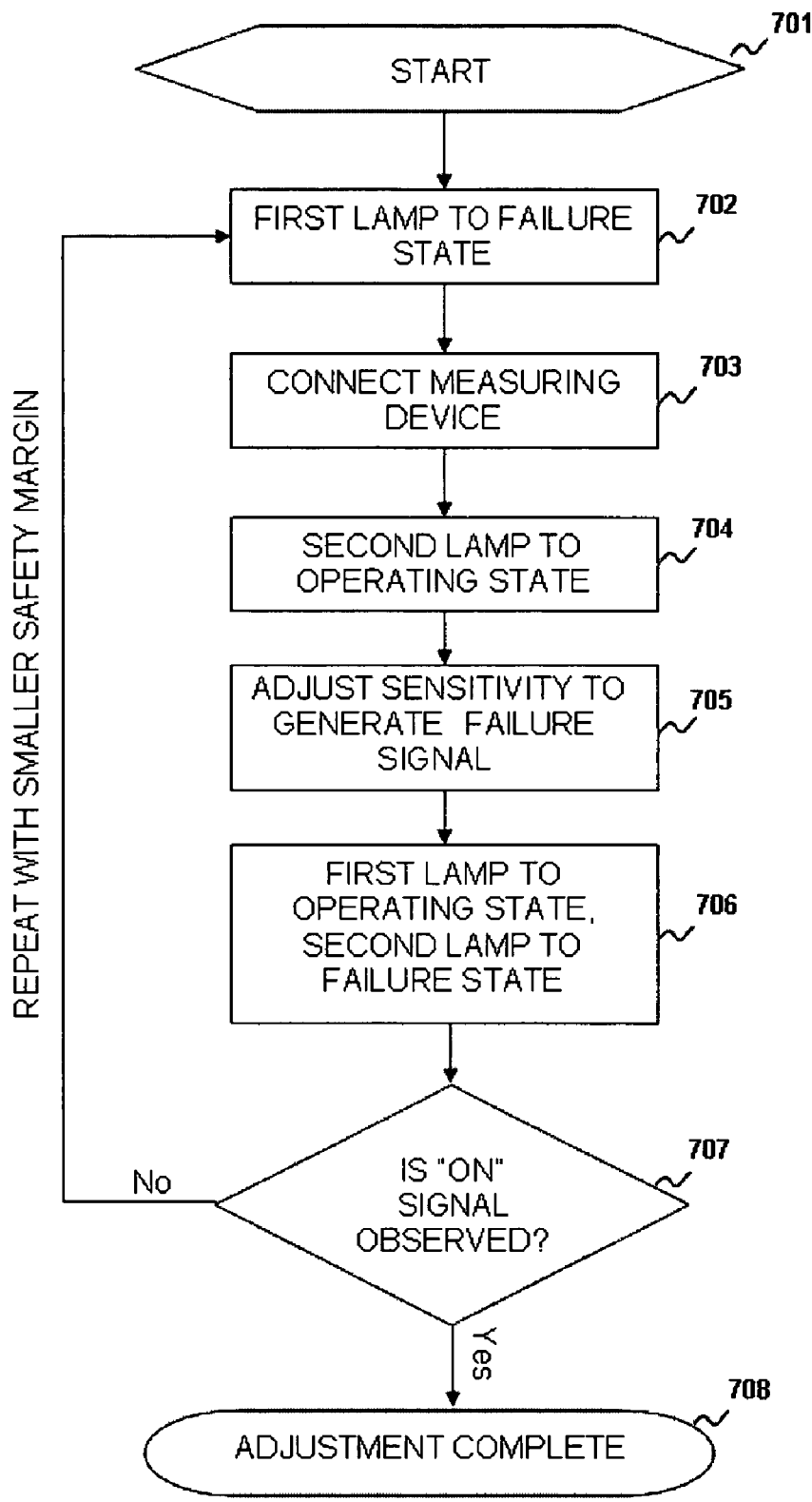
FIG. 7 is a flow chart of steps performed in another adjusting process, consistent with an embodiment of the present invention.

First light sensing apparatus 370 comprises a phototransistor circuit having adjustable sensitivity. First light sensing apparatus 370 is further configured to provide signals to a sensor output based upon the current state of first lamp 310 and the current state of second lamp 320. In one embodiment, the sensitivity of the phototransistor circuit of first light sensing apparatus 370 is adjusted to generate an "ON" signal when the first lamp is in the first lamp operating state and the second lamp is in the second lamp operating state; to generate the "ON" signal when the first lamp is in the first lamp operating state and the second lamp is in the second lamp failure state; to generate a failure signal when the first lamp is in the first lamp failure state and the second lamp is in the second lamp operating state; and to generate the failure signal when the first lamp is in the first lamp failure state and the second lamp is in the second lamp failure state. As illustrated in FIG. 7, in UV lamp system 300, the adjusting the sensitivity of the phototransistor circuit of first light sensing apparatus 370 (at step 701) could be accomplished for applications where highly reflective material is processed under the UV lamps, for example through a process comprising the following steps:

1) First lamp 310 is put into the first lamp failure state (step 702).
2) A multi-meter or other voltage measuring device may be connected to first light sensing apparatus 370 (step 703) to measure the output signal (which is available at the sensor output). This signal will be observed while the sensitivity of the phototransistor circuit is adjusted. (One skilled in the art would appreciate that the connection of the measuring device does not have to occur in this precise sequence in order to be consistent with the present invention.)
3) Second Lamp 320 is put into the second lamp operating state (step 704).
4) The sensitivity of the phototransistor circuit of first lamp 310 may be adjusted (step 705) to create the desired failure signal (that is, the sensitivity of the phototransistor circuit may be adjusted until the sensor output is at the desired level). In one embodiment, the phototransistor circuit can be adjusted so the sensor output level is beyond this threshold by a safety margin, e.g. 0.5 VDC. (The sensor output level may be adjusted above or below the threshold value respectively depending if the light sensing apparatus is inverting or non-inverting. Such adjustment would be understood by one of ordinary skill in the art.)
5) First Lamp 310 is then put in the first lamp operating state, and second lamp 320 is put into the second lamp failure state (step 706). The sensor output of first lamp 310 is observed to ensure that first light sensing apparatus now provides the "ON" signal (step 707). (If the first light sensing apparatus does not provide the "ON" signal, steps 1-4 should be repeated but this time a smaller safety margin should be employed). If the first light sensing apparatus now provides the "ON" signal, the adjustment is complete (step 708).

Figure 8:
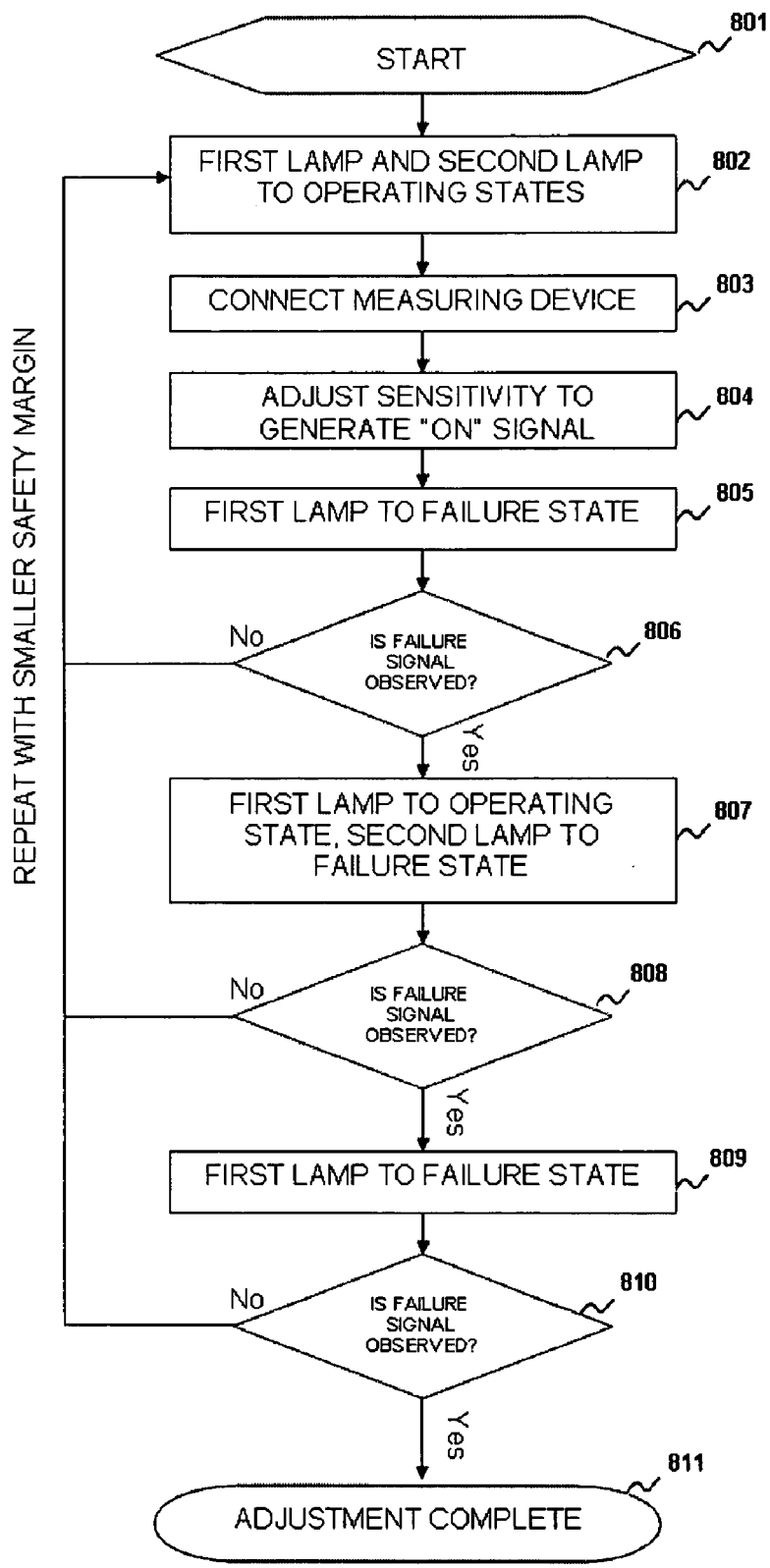
FIG. 8 is a flow chart of steps performed in another adjusting process, consistent with an embodiment of the present invention.

The sensitivity of the phototransistor circuit of the first light sensing apparatus 370 can be adjusted for other modes of operation. In another embodiment, the sensitivity the phototransistor circuit of the first light sensing apparatus 370 may be adjusted to generate an "ON" signal when the first lamp is in the first lamp operating state and the second lamp is in the second lamp operating state; to generate a failure signal when the first lamp is in the first lamp failure state and the second lamp is in the second lamp operating state; to generate the failure signal when the first lamp is in the first lamp operating state and the second lamp is in the second lamp failure state; and to generate the failure signal when the first lamp is in the first lamps failure state and the second lamp is in the second lamp failure state. As illustrated in FIG. 8, to meet these requirements, the adjusting the sensitivity of the phototransistor circuit of first light sensing apparatus 370 (at step 801) could be accomplished, for example, through a process comprising the following steps:

1) First lamp 310 and second lamp 320 are put into the first and second lamp operating states (step 802).
2) A multi-meter or other voltage measuring device may be connected (step 803) to measure the output signal to first light sensing apparatus 370 (which is available at the sensor output). This signal will be observed while the sensitivity of the phototransistor circuit is adjusted. (One skilled in the art would appreciate that the connection of the measuring device does not have to occur in this precise sequence in order to be consistent with the present invention.)
3) The sensitivity of the phototransistor circuit of first lamp 310 may be adjusted (step 804) to create the desired "ON" signal (that is, the sensitivity of the phototransistor circuit may be adjusted until the sensor output is at the desired level). In one embodiment, the phototransistor circuit can be adjusted so the sensor output level is beyond this threshold by a safety margin, e.g. 0.5 VDC. (The sensor output level may be adjusted above or below the threshold value respectively depending if the light sensing apparatus is inverting or non-inverting. Such adjustment would be understood by one of ordinary skill in the art.)
4) First Lamp 310 is then put in the first lamp failure state (step 805). Second lamp 320 remains in the second lamp operating state. The sensor output of first lamp 310 is observed (step 806) to ensure that first light sensing apparatus now provides the failure signal. (If the first light sensing apparatus does not provide the failure signal, steps 1-4 should be repeated but this time a smaller safety margin should be employed).
5) First Lamp 310 is then put into the first lamp operating state and the second lamp 320 is then put in the second lamp failure state (step 807). The sensor output of first lamp 310 is observed to ensure that first light sensing apparatus still provides the failure signal (step 808). (If the first light sensing apparatus does not provide the failure signal, steps 1-5 should be repeated but this time a smaller safety margin should be employed).
6) First Lamp 310 and second lamp 320 are then put into the first lamp and second lamp failure states (step 809). The sensor output of first lamp 310 is observed (step 810) to ensure that first light sensing apparatus still provides the failure signal. (If the first light sensing apparatus does not provide the failure signal, steps 1-6 should be repeated but this time a smaller safety margin should be employed). If the light sensing apparatus still provides the failure signal the adjustment is complete (step 811).

Other embodiments consistent with the above sequence of steps would be readily apparent to one skilled in the art.

Figure 4:
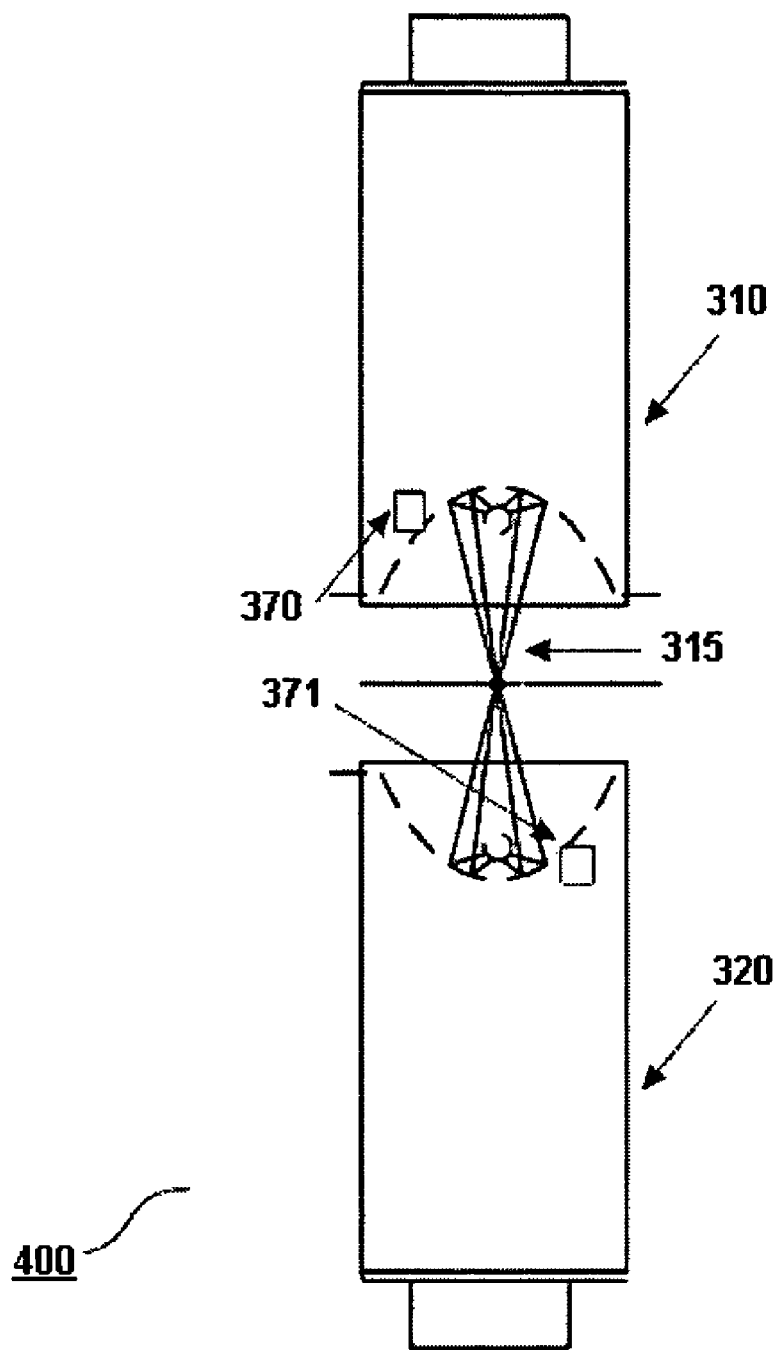
FIG. 4 is a UV lamp system consistent with an embodiment of the present invention.

Moreover, in addition to the arrangements of first lamp and the second lamp as described in FIG. 3, other arrangements are possible. For example, FIG. 4 shows a UV lamp system 400 consistent with another embodiment of the present invention. UV lamp system 400 can be adjusted through a process similar to the any of the aforementioned adjustment processes. Further, other spatial arrangements are possible. The light sensing apparatus can be adjusted to the correct sensitivity for a first and second lamp in any relative spatial orientation. The first and second lamp need not be substantially parallel and adjacent or substantially parallel and facing, as shown in FIG. 3 and FIG. 4 respectively.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A method for detecting radiant energy with a light sensing apparatus, the light sensing apparatus comprising a phototransistor, a sensitivity adjusting circuit and a signal conditioning circuit having a sensor output terminal, the method comprising:
    determining a first power level and a second power level lower than the first power level of a UV lamp system;
    detecting radiant energy from the UV lamp system at the first power level and at the second power level, respectively; and
    adjusting the light sensing apparatus so that the light sensing apparatus is able to provide a first signal that corresponds to the first power level and a second signal that corresponds to the second power level, wherein:
    the phototransistor has a first terminal coupled to the sensor output terminal, a second terminal coupled to ground and a third terminal coupled to the sensitivity adjusting circuit, the sensitivity adjusting circuit includes:
        a first capacitor coupled to the third terminal; and
        an adjustable resistance coupled to the third terminal in parallel with the capacitor and
    sensitivity of the phototransistor circuit is adjustable by the adjustable resistance.

2. The method of claim 1, wherein:
    the phototransistor circuit comprises a bipolar junction transistor having a base, a collector and an emitter, and
    the first terminal is the collector, the second terminal is the emitter and the third terminal is the base.

3. The method of claim 1, wherein the adjustable resistance comprises a potentiometer.

4. The method of claim 1, wherein the signal conditioning circuit comprises:
    a second capacitor coupled between the second terminal and the sensor output terminal, wherein a first end of the second capacitor is coupled to the second terminal and a second end of the second capacitor is coupled to the sensor output terminal; and
    a resistor coupled between the first terminal and the sensor output terminal, wherein a first end of the resistor is coupled to the first terminal and a second end of the resistor is coupled to the sensor output terminal.

5. The method of claim 4, wherein the light sensing apparatus further comprises a source resistor coupled between the sensor output terminal and a power-source.

6. The method of claim 1, wherein the signal conditioning circuit comprises a low-pass filter.

7. The method of claim 1, wherein the adjusting step comprises:
    measuring the first signal; and
    adjusting the adjustable resistance.

8. The method of claim 1, further comprising:
    changing the light sensing apparatus into an adjustment mode.

9. A method for detecting radiant energy with a light sensing apparatus, the light sensing apparatus comprising a phototransistor, a sensitivity adjusting circuit and a signal conditioning circuit having a sensor output terminal, the method comprising:
    configuring an UV lamp to provide radiant energy at or above a first power level;
    detecting certain of the radiant energy provided by the UV lamp system;
    measuring a first signal of the light sensing apparatus that corresponds to the radiant energy at or above the first power level;
    adjusting the light sensing apparatus so that the first signal is at a first signal ON level;
    configuring the UV lamp system to provide radiant energy at a second power level, where the second power level is less than the first power level;
    measuring the first signal of the light sensing apparatus that corresponds to the radiant energy at the second power level; and
    determining if the first signal is at a first signal failure level, wherein:
    the phototransistor has a first terminal coupled to the sensor output terminal, a second terminal coupled to ground and a third terminal coupled to the sensitivity adjusting circuit,
    the sensitivity adjusting circuit includes:
        a first capacitor coupled to the third terminal; and
        an adjustable resistance coupled to the third terminal in parallel with the capacitor and
    sensitivity of the phototransistor circuit is adjustable by the adjustable resistance.

10. The method of claim 9, wherein the first signal ON level is greater than the first signal failure level.

11. The method of claim 9, wherein the first signal ON level is less than the first signal failure level.

12. The method of claim 9, wherein adjusting the light sensing apparatus further includes adjusting the light sensing apparatus so that the first signal is above the first signal ON level.

13. The method of claim 9, wherein adjusting the light sensing apparatus further includes adjusting the light sensing apparatus so that the first signal is below the first signal ON level.

14. The method of claim 9, wherein if the first signal is not at the first signal failure level, the method further performs steps of:
    configuring the UV lamp system to provide radiant energy at or above the first power level;
    detecting certain of the radiant energy provided by the UV lamp system;
    measuring the first signal of the light sensing apparatus that corresponds to the radiant energy at or above the first power level; and
    adjusting the light sensing apparatus so that the first signal is at a first signal ON level.

15. A method for detecting radiant energy with a light sensing apparatus, the light sensing apparatus comprising a phototransistor circuit configured with an adjustable sensitivity and a signal conditioning circuit, the method comprising:
    configuring a first UV lamp system to provide radiant energy at a first UV lamp system failure power level;
    configuring a second UV lamp system to provide radiant energy at or above a second UV lamp system ON power level;
    detecting at least certain of the radiant energy provided by the second UV lamp system at or above the second UV lamp system ON power level;
    measuring a first signal of the light sensing apparatus that corresponds to the radiant energy provided by the first UV lamp system at the first UV lamp system failure power level and the second UV lamp system at or above the second UV lamp system ON power level;
    adjusting the light sensing apparatus so that the first signal is at a first signal failure level;

configuring the first UV lamp system to provide radiant energy at or above a first UV lamp system ON power level, where the power provided at the first UV lamp system ON power level is greater than the power provided at first UV lamp system failure power level;
detecting at least certain of the radiant energy provided by the first UV lamp system at or above the first UV lamp system power level;
configuring the second UV lamp system to provide radiant energy at a second UV lamp system failure power level, where the power provided at the second UV lamp system failure power level is less than the power provided at the second UV lamp system ON power level;
measuring the first signal of the light sensing apparatus that corresponds to the radiant energy of the first UV lamp system at or above the first UV lamp system ON power level and the second UV lamp system at the second UV lamp system failure power level; and
determining if the first signal is at a first signal ON level.

16. The method of claim 15, wherein the first signal ON level is greater than the first signal failure level.

17. The method of claim 15, wherein the first signal ON level is less than the first signal failure level.

18. The method of claim 15, wherein adjusting the light sensing apparatus so that the first signal is at a first signal failure level further includes adjusting the light sensing apparatus so that the first signal is above the first signal failure level.

19. The method of claim 15, wherein adjusting the light sensing apparatus so that the first signal is at a first signal failure level further includes adjusting the light sensing apparatus so that the first signal is below the first signal failure level.

20. The method of claim 15, wherein the radiant energy at the first UV lamp system failure power level is substantially no radiant energy.

21. The method of claim 15, wherein if the first signal is not at the ON signal level, the method further performs steps of:
configuring the first UV lamp system to provide radiant energy at the first UV lamp system failure power level;
configuring the second UV lamp system to provide radiant energy at or above the second UV lamp system ON power level;
detecting at least certain of the radiant energy provided by the second UV lamp system at or above the second UV lamp system ON power level;
measuring the first signal of the light sensing apparatus that corresponds to the radiant energy provided by the first UV lamp system at the first UV lamp system failure power level and the second UV lamp system at or above the second UV lamp system ON power level; and
adjusting the light sensing apparatus so that the first signal is at the first signal failure level.

22. A method for detecting radiant energy with a light sensing apparatus, the light sensing apparatus comprising a phototransistor circuit configured with an adjustable sensitivity and a signal conditioning circuit, the method comprising:
configuring a first UV lamp system to provide radiant energy at or above a first UV lamp system ON power level;
configuring a second UV lamp system to provide radiant energy at or above a second UV lamp system ON power level;
detecting certain of the radiant energy provided by the first UV lamp system at or above the first UV lamp system ON power level and the second UV lamp system at or above the second UV lamp system ON power level;
measuring a first signal of the light sensing apparatus that corresponds to the radiant energy provided by the first UV lamp system at or above the first UV lamp system ON power level and the second UV lamp system at or above the second UV lamp system ON power level;
adjusting the light sensing apparatus so that the first signal is at a first signal ON level;
configuring the first UV lamp system to provide radiant energy at a first UV lamp system failure power level, where the power provided at the first UV lamp system failure power level is less than the power provided at the first UV lamp system ON power level;
measuring the first signal of the light sensing apparatus that corresponds to the radiant energy of the first UV lamp system at the first UV lamp system failure power level and the second UV lamp system at or above the second UV lamp system ON power level; and
determining if the first signal is at a first signal failure level.

23. The method of claim 22, further comprising:
configuring the first UV lamp system to provide radiant energy at or above the first UV lamp system ON level;
configuring the second UV lamp system to provide radiant energy at a second UV lamp system failure power level, where the power provided at the second UV lamp system failure power level is less than the power provided at the second UV lamp system ON power level;
measuring the first signal of the light sensing apparatus that corresponds to the radiant energy of the first UV lamp system at or above the first UV lamp system ON power level and the second UV lamp system at the second UV lamp system failure power level; and
determining if the first signal is at the first signal failure level.

24. The method of claim 23, further comprising:
configuring the first UV lamp system to provide radiant energy at the first UV lamp system failure power level;
configuring the second UV lamp system to provide radiant energy at a second UV lamp system failure power level, where the power provided at the second UV lamp system failure power level is less than the power provided at the second UV lamp system ON power level;
measuring the first signal of the light sensing apparatus that corresponds to the radiant energy of the first UV lamp system at the first UV lamp system failure power level and the second UV lamp system at the second UV lamp system failure power level; and
determining if the first signal is at the first signal failure level.

25. The method of claim 24, wherein the first signal ON level is greater than the first signal failure level.

26. The method of claim 24, wherein the first signal ON level is less than the first signal failure level.

27. The method of claim 24, wherein adjusting the light sensing apparatus further includes adjusting the light sensing apparatus so that the first signal is above the first signal ON level.

28. The method of claim 24, wherein adjusting the light sensing apparatus further includes adjusting the light sensing apparatus so that the first signal is below the first signal ON level.

29. The method of claim 24, wherein if the first signal is not at the first signal failure level, the method further performs steps of:
configuring the first UV lamp system to provide radiant energy at or above the first UV lamp system ON power level;

configuring the second UV lamp system to provide radiant energy at or above the second UV lamp system ON power level;

detecting certain of the radiant energy provided by the first UV lamp system at or above the first UV lamp system ON power level and the second UV lamp system at or above the second UV lamp system ON power level;

measuring the first signal of the light sensing apparatus that corresponds to the radiant energy provided by the first UV lamp system at or above the first UV lamp system ON power level and the second UV lamp system at or above the second UV lamp system ON power level; and adjusting the light sensing apparatus so that the first signal is at the first signal ON level.

30. A UV lamp system comprising:

a first lamp configured to provide radiation output at or above a first lamp operational radiation output to an output region when in a first lamp operating state and to provide less than the first lamp operational radiation output to the output region when in a first lamp failure state; and a second lamp configured to provide radiation output at or above a second lamp operational radiation output to the output region when in a second lamp operating state and to provide less than the second lamp operational radiation output to the output region when in a second lamp failure state; and a first light sensing apparatus comprising a phototransistor, a sensitivity adjusting and a signal conditioning circuit having a sensor output terminal, the first light sensing apparatus being provided for the first lamp and configured to provide signals to the sensor output based on a state of the first lamp and a state of the second lamp, wherein:

the first light sensing apparatus in the output region is configured to generate an ON signal when the first lamp is in the first lamp operating state and the second lamp is in the second lamp operating state; and the first light sensing apparatus in the output region is further configured to generate a failure signal when the first lamp is in the first lamp failure state and the second lamp is in the second lamp failure state.

31. The UV lamp system of claim 30, wherein:

the first light sensing apparatus in the output region is further configured to generate the failure signal when the first lamp is in the first lamp failure state and the second lamp is in the second lamp operating state; and the first light sensing apparatus in the output region is further configured to generate the ON signal when the first lamp is in the first lamp operating state and the second lamp is in the second lamp failure state.

32. The UV lamp system of claim 30, wherein:

the first light sensing apparatus in the output region is further configured to generate the ON signal when the first lamp is in the first lamp failure state and the second lamp is in the second lamp operating state; and the first light sensing apparatus in the output region is further configured to generate the ON signal when the first lamp is in the first lamp operating state and the second lamp is in the second lamp failure state.

33. The UV lamp system of claim 30, wherein the ON signal level is greater than the failure signal level.

34. The UV lamp system of claim 30, wherein the ON signal level is less than the failure signal level.

35. The UV lamp system of claim 30, wherein the first light sensing apparatus is adjusted to provide a signal above the ON signal.

36. The UV lamp system of claim 30, wherein the first light sensing apparatus is adjusted to provide a signal below the ON signal.

37. The UV lamp system of claim 30, wherein:

the phototransistor has a first terminal coupled to the sensor output terminal, a second terminal coupled to ground and a third terminal coupled to the sensitivity adjusting circuit, the sensitivity adjusting circuit includes:
 a first capacitor coupled to the third terminal; and
 an adjustable resistance coupled to the third terminal in parallel with the capacitor and
sensitivity of the phototransistor circuit is adjustable by the adjustable resistance.

38. The UV lamp system of claim 37, wherein:

the phototransistor circuit comprises a bipolar junction transistor having a base, a collector and an emitter, and the first terminal is the collector, the second terminal is the emitter and the third terminal is the base.

39. The UV lamp system of claim 37, wherein the adjustable resistance comprises a potentiometer.

40. The UV lamp system of claim 37, wherein the signal conditioning circuit comprises:

a second capacitor coupled between the second terminal and the sensor output terminal, wherein a first end of the second capacitor is coupled to the second terminal and a second end of the second capacitor is coupled to the sensor output terminal;

a resistor coupled between the first terminal and the sensor output terminal, wherein a first end of the resistor is coupled to the first terminal and a second end of the resistor is coupled to the sensor output terminal.

41. The UV lamp system of claim 37, wherein the signal conditioning circuit comprises a low-pass filter.

42. The UV lamp system of claim 30, wherein the phototransistor circuit comprises a bipolar junction transistor.

43. The UV lamp system of claim 30, wherein the signal conditioning circuit comprises a low-pass filter.

44. The UV lamp system of claim 30, further comprising a second light sensing apparatus provided for the second lamp.

* * * * *